United States Patent
Wu

(10) Patent No.: US 9,834,555 B2
(45) Date of Patent: *Dec. 5, 2017

(54) METHOD FOR TREATING PAIN SYNDROME AND OTHER DISORDERS

(71) Applicant: VM Therapeutics LLC, Fremont, CA (US)

(72) Inventor: Jay Jie-Qiang Wu, Fremont, CA (US)

(73) Assignee: VM Therapeutics LLC., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/210,102

(22) Filed: Jul. 14, 2016

(65) Prior Publication Data

US 2016/0318930 A1 Nov. 3, 2016

Related U.S. Application Data

(60) Continuation of application No. 14/617,368, filed on Feb. 9, 2015, now Pat. No. 9,402,848, which is a division of application No. 14/481,398, filed on Sep. 9, 2014, now Pat. No. 8,980,900, which is a continuation of application No. 12/870,327, filed on Aug. 27, 2010, now Pat. No. 8,865,727, which is a continuation-in-part of application No. PCT/US2009/035319, filed on Feb. 26, 2009.

(60) Provisional application No. 61/032,669, filed on Feb. 29, 2008.

(51) Int. Cl.
| | |
|---|---|
| *A61K 31/519* | (2006.01) |
| *C07D 471/04* | (2006.01) |
| *A61K 31/4184* | (2006.01) |
| *A61K 31/498* | (2006.01) |
| *C07D 401/06* | (2006.01) |
| *C07D 513/04* | (2006.01) |
| *A61K 31/517* | (2006.01) |
| *A61K 9/00* | (2006.01) |
| *A61K 9/06* | (2006.01) |

(52) U.S. Cl.
CPC .......... *C07D 471/04* (2013.01); *A61K 9/0014* (2013.01); *A61K 9/06* (2013.01); *A61K 31/4184* (2013.01); *A61K 31/498* (2013.01); *A61K 31/517* (2013.01); *A61K 31/519* (2013.01); *C07D 401/06* (2013.01); *C07D 513/04* (2013.01)

(58) Field of Classification Search
None
See application file for complete search history.

(56) References Cited

U.S. PATENT DOCUMENTS

| | | | |
|---|---|---|---|
| 4,342,870 A | 8/1982 | Kennis et al. | |
| 4,680,296 A | 7/1987 | Manoury et al. | |
| 5,618,720 A | 4/1997 | Ellis et al. | |
| 5,686,241 A | 11/1997 | Ellis et al. | |
| 5,710,250 A | 1/1998 | Ellis et al. | |
| 5,726,035 A | 3/1998 | Jay et al. | |
| 5,792,846 A | 8/1998 | Harpold et al. | |
| 5,846,757 A | 12/1998 | Harpold et al. | |
| 5,851,824 A | 12/1998 | Harpold et al. | |
| 5,874,236 A | 2/1999 | Harpold et al. | |
| 5,876,958 A | 3/1999 | Harpold et al. | |
| 5,925,634 A | 7/1999 | Olney | |
| 6,013,474 A | 1/2000 | Ellis et al. | |
| 6,057,114 A | 5/2000 | Akong et al. | |
| 6,096,514 A | 8/2000 | Harpold et al. | |
| 6,156,741 A | 12/2000 | Durant et al. | |
| 6,537,520 B1 | 3/2003 | Rajopadhye et al. | |
| 8,865,727 B2 | 10/2014 | Wu | |
| 8,980,900 B2 | 3/2015 | Wu | |
| 9,402,848 B2 | 8/2016 | Wu | |
| 2003/0134840 A1 | 7/2003 | Baxter et al. | |
| 2004/0266808 A1 | 12/2004 | Kamen et al. | |
| 2005/0032827 A1 | 2/2005 | Oksenberg et al. | |
| 2006/0154929 A1 | 7/2006 | Anker et al. | |
| 2007/0259867 A1 | 11/2007 | Cho et al. | |
| 2008/0194631 A1 | 8/2008 | Trovero et al. | |
| 2009/0325975 A1 | 12/2009 | Buschmann | |
| 2011/0053960 A1 | 3/2011 | Wu | |
| 2014/0378476 A1 | 12/2014 | Wu | |
| 2015/0150875 A1 | 6/2015 | Wu | |

FOREIGN PATENT DOCUMENTS

| | | |
|---|---|---|
| CA | 2051840 A1 | 3/1993 |
| EP | 0037265 A1 | 10/1981 |
| JP | S56-150091 A | 3/1983 |
| WO | WO 99/28342 A3 | 8/1999 |
| WO | WO 99/59409 A1 | 11/1999 |
| WO | WO 00/02455 A1 | 1/2000 |
| WO | WO 00/15845 A1 | 3/2000 |
| WO | WO 00/59882 A1 | 10/2000 |
| WO | WO 01/19845 A1 | 3/2001 |
| WO | WO 01/02561 A3 | 6/2001 |
| WO | WO 01/74359 A1 | 10/2001 |
| WO | WO 02/102387 A1 | 12/2002 |

(Continued)

OTHER PUBLICATIONS

"Beilstein Handbook of Organic Chemistry," Beilstein Institute of Organic Chemistry, Frankfurt, Germany, 6 pages.
"International Search Report," in PCT appl. No. PCT/US2009/035319, dated May 29, 2009, 4 pages.
"Written Opinion of the International Searching Authority," in PCT appl. No. PCT/US2009/035319, dated May 29, 2009, 5 pages.
"International Preliminary Report on Patentability," in PCT appl. No. PCT/US2009/035319, dated Aug. 31, 2010, 6 pages.
"Theilheimer's Synthetic Methods of Organic Chemistry," vols. 1-45, Karger (1991).
Anderson, A.C., "The process of structure-based drug design." Chemistry & Biology (2003); 10.9: 787-797.
Bhattacharjee, et al. "T-type calcium channels facilitate insulin secretion by enhancing general excitability in the insulin-secreting beta-cell line, INS-1.", Endocrinology (1997); 138: 3735-3740.

(Continued)

*Primary Examiner* — Craig Ricci
(74) *Attorney, Agent, or Firm* — Cooley LLP

(57) ABSTRACT

The present invention provides the use of certain compounds to treat peripheral or central pain syndrome and other disorders associated with the T-type calcium ion channels.

19 Claims, 3 Drawing Sheets

(56) References Cited

FOREIGN PATENT DOCUMENTS

| WO | WO 03/007953 A1 | 1/2003 |
|---|---|---|
| WO | WO 03/106660 A2 | 12/2003 |
| WO | WO 2004/048364 A1 | 6/2004 |
| WO | WO 2005/041971 A1 | 5/2005 |
| WO | WO 2006/010587 A1 | 2/2006 |
| WO | WO 2006/018538 A1 | 2/2006 |
| WO | WO 2006/122035 A3 | 3/2007 |
| WO | WO 2007/025613 A2 | 3/2007 |
| WO | WO 2007/070679 A2 | 6/2007 |
| WO | WO 2008/112715 A2 | 9/2008 |
| WO | WO 2008/112715 A3 | 11/2008 |
| WO | WO 2007/070679 A3 | 1/2009 |
| WO | WO 2009/108798 A1 | 9/2009 |

OTHER PUBLICATIONS

Bourinet et al, "Silencing of the Cav3.2 T-type calcium channel gene in sensory neurons demonstrates its major role in nociception", EMBO J. (2005); 24: 315-324.

Bundgaard et al., "Bioreversible derivatization of the pyroglutamyl by N-acylation and Naminomethylation to effect protection against pyroglutamyl aminopeptidase", J. Pharm. Sci. (1989); 78: 122-126.

Chemin et al., "Specific contribution of human T-type calcium channel isotypes (alpha(1G), alpha(1H) and alpha(1I)) to neuronal excitability." J. Physiol. (2002); 540: 3-14.

Ellis et al., "The rat formalin test: Can it predict neuropathic pain treatments". Proceedings of Measuring Behavior (2008); pp. 324-325.

Feiser et al., "Reagents for Organic Synthesis," vols. 1-21, Wiley Interscience (2006).

Gogas. K. R., et al. "Effects of the T-type calcium channel blocker, Elhosuximide. In rodent models of acute and chronic pain", Abstract. IASP 10th World Congress on Pain (2002); San Diego, CA.

Green et al., "Protective Groups in Organic Chemistry", Wiley, 2nd ed. (1991).

Greene & Wuts, "Protective Groups in Organic Synthesis," Wiley Interscience (1999), 2 pages.

Han, "Advances in Characterization of Pharmaceutical Hydrates," Trends in Bio/Pharmaceutical Industry (2006); 2(3): 25-29.

Hare et al., "Effect of 5-hydroxytryptamine type-2 receptor blockade on pulmonary function in calves with experimentally induced Pasteurella haemolytica pneumonia," Am. J. Vet. Res. (1996); 57(7): 1034-1039.

Harrison et al., "Compendium of Synthetic Organic Methods", vols. 1-8, John Wiley and Sons, 1971-1996.

Hong et al., "Topical ketanserin attenuates hyperalgesia and inflammation in arthritis in rats," Pain (2006); 124: 27-33.

Huguenard et al. "Intrathalamic rhythmicity studied in vitro: nominal T-current modulation causes robust antioscillatory effects", J Neuroscience (1994); 14: 5485-5502.

Joksovic, et al., "CaV3.2 is the major molecular substrate for redox regulation of T-type Ca2+ channels in the rat and mouse thalamus," J Physiol (2006); 574(2): 415-430.

Kyriakides et al., "Intracoronary Ketanserin Augments Coronary Collateral Blood Flow and Decreases Myocardial Ischemia During Balloon Angioplasty," Cardiovasc. Drugs Ther. (1999); 13: 415-422.

Larock, "Comprehensive Organic Transformations," VCH Publishers, 1989.

Lee et al., "Cloning and Expression of a Novel Member of the Low Voltage-Activated T-Type Calcium Channel Family," J. Neuroscience, 1999, vol. 19(6), 1912-1921.

March, "Advanced Organic Chemistry," Wiley Interscience, 1991.

Naghdi et al., "The Effect of Ketanserin and Pirenperone Injected into the CA1 Region on Spatial Discrimination," Iran. Biomed. J. (2001); 5(4): 141-147.

Nakanishi et al., "Involvement of peripheral 5-HT2A receptor activation in inflammatory pain," Nippon Rinsho (2001); vol. 59(9): 1675-1680 (Abstract Only).

Nitanda et al., "Contribution of the peripheral 5-HT2A receptor to mechanical hyperalgesia in a rat model of neuropathic pain," Neurochem. Int. (2005); 47: 394-400.

Office Action, European Application No. 09715280.5, dated Nov. 5, 2015, 4 pages.

Office Action, Japanese Application Serial No. 2010-548872, dated Sep. 22, 2014, 2 pages.

Office Action, Japanese Application Serial No. 2015-067995, dated Jun. 15, 2015, 4 pages. (English Translation).

Osterberg et al. "Adherance to Medicine", Drug Future (2005); 30(6): 573-580.

Paquette, "Encyclopedia of Reagents for Organic Synthesis," 3d Edition, John Wiley & Sons, 1995.

Saller et al., "5-HT2 Receptor Blockade by ICI 169,369 and other 5-HT2 Antagonists Mudulates the Effects of D-2 Dopamine Receptor Blockade," J. Pharmacol. Exp. Ther. (1990); 269(3): 1162-1170.

Stella et al., "Prodrugs: Challenges and Rewards, Part I." Biotechnology: Pharmaceutical Aspects (2007); p. 24, 4 pages.

Supplementary European Search Report, EP Appl. No. 09715280.5, 18 pages (dated Sep. 3, 2012).

Thiel, K.A., "Structure-aided drug design's next generation." Nature Biotechnology (2004); 22(5): 513-519.

Todorovic et al., "Pharmacological Properties of T-Type Ca2+ Current in Adult Rat Sensory Neurons: Effects of Anticonvulsant and Anesthetic Agents", The Journal of Neurophysiology (1998); 79(1): 240-252.

Trost et al., "Comprehensive Organic Synthesis," Pergamon Press, 1991.

Vippagunta et al., "Crystalline solids," Adv. Drug. Deliv. Rev. 48:3-26 (2001).

Xia, et al., "Generation and Characterization of a Cell Line with Inducible Expression of Cav3.2 (TType) Channels," Assay and Drug Development Tech. (2003); 1(5): 637-645.

Yun Jeong Choe et al., "Synthesis and SAR Study of T-Type Calcium Channel Blockers. Part II." Arch. Pharm. Chem. Life. Sci. (2008); 341: 661-664.

Extended European Search Report, EP Appl. No. 16170030.7, dated Nov. 14, 2016, 11 pages.

Kiefel, Jacqueline M., et al. "Reduction in opioid and non-opioid forms of swim analgesia by 5-HT 2 receptor antagonists." Brain Research (189); 500.1: 231-240.

Paul, Dennis, and Pinel, John, P.J. "Pirenperone does not attenuate morphine analgesia in spinal rats." Psychopharmacology (1990); 100.1: 98-101.

Paul, Dennis, and Phillips, Anthony G. "Selective effects of pirenperone on analgesia produced by morphine or electrical stimulation at sites in the nucleus raphe magnus and periaqueductal gray." Psychopharmacology (1986); 88.2: 172-176.

Paul, Dennis,et al. "Attenuation of morphine analgesia by the S2 antagonists, pirenperone and ketanserin." Pharmacology Biochemistry and Behavior (1989); 31.3: 641-647.

Vonvoigtlander, Philip F., et al. "Kappa opioid analgesia is dependent on serotonergic mechanisms." Journal of Pharmacology and Experimental Therapeutics (1984); 231.2: 270-274.

METHOD FOR TREATING PAIN SYNDROME AND OTHER DISORDERS

CROSS-REFERENCE TO RELATED APPLICATIONS

This application is a Continuation application of U.S. patent application Ser. No. 14/617,368, filed on Feb. 9, 2015, which is itself a Divisional application of U.S. patent application Ser. No. 14/481,398, filed on Sep. 9, 2014, and issued as U.S. Pat. No. 8,980,900 on Mar. 17, 2015, which is itself a Continuation application of U.S. patent application Ser. No. 12/870,327, filed on Aug. 27, 2010, and issued as U.S. Pat. No. 8,865,727, on Oct. 21, 2014, which is itself a Continuation-in-Part application of International Application No. PCT/US2009/035319, filed on Feb. 26, 2009, which in turn claims the benefit of priority to U.S. Provisional Patent Application No. 61/032,669, filed on Feb. 29, 2008, the contents of each of which are hereby incorporated by reference in their entirety for all purposes.

FIELD OF THE INVENTION

The present invention relates to the use of 1-heteroalkyl derivatives of 4-benzoylpiperdines for treating diseases and conditions associated with the T-type calcium ion channels.

BACKGROUND OF THE INVENTION

Calcium ion channels are membrane-spanning, multi-subunit proteins that allow $Ca^{2+}$ entry from the external milieu and concurrent depolarization of the cell's membrane potential, and play a central role in neurotransmitter release. Traditionally calcium ion channels have been classified based on their functional characteristics such as low voltage or high voltage activated and their kinetics (L, T, N, P, Q). The ability to clone and express the calcium ion channel subunits has lead to an increased understanding of the channel composition that produces these functional responses. Calcium ion channels can be classified into a number of types and subtypes, for example L-(or Cav1), P/Q-(or Cav2.1), N-(or Cav2.2), R-(Cav2.3) and T-(or Cav3) types. T-type calcium ion channels can, for example, be molecularly, pharmacologically and electrophysiologically sub-classified into α1G (or Cav3.1), α1H (or Cav3.2), and α1I (or Cav3.3) T channels from various warm blooded animals including rat. The "T-type" (or "low voltage-activated") calcium ion channels are so named because their openings are of briefer duration (T=transition) than the longer (L=long-lasting) openings of the L-type calcium ion channels. The L, N, P and Q-type channels activate at more positive potentials (high voltage activated) and display diverse kinetics and voltage-dependent properties. See e.g. Catterall, Annu. Rev. Cell Dev. Biol. 16, 521-55, (2000) and Perez-Reyes Physiol. Rev. 83, 117-161, (2003).

The pharmacology of the three subfamilies of calcium ion channels is quite distinct from each other. The type I Cav1 (L-type) channels are distributed within cardiac muscle, smooth muscle including blood vessels, intestine, lung, uterus, skeletal muscale, endocrine cells, and are the molecular targets of the organic calcium ion channels blockers used widely in the therapy of cardiovascular diseases.

The type II Cav2 (P, Q, N. R) channels are in neurons, heart, etc. They are relatively insensitive to dihydropyridine calcium ion channels blockers, but these channels are specifically blocked with high affinity by peptide toxins from spiders and marine snails. The N type $Ca^{2+}$ channel (Cav2.2) is highly expressed at the presynaptic nerve terminals of the dorsal root ganglion as it forms a synapse with the dorsal horn neurons in lamina I and II. These neurons in turn have large numbers of N type $Ca^{2+}$ channels at their presynaptic terminals as they synapse onto second and third order neurons. This pathway is very important in relaying pain information to the brain. The N type $Ca^{2+}$ channel has been validated in man by intrathecal infusion of the toxin Ziconotide for the treatment of intractable pain, cancer pain, opioid resistant pain, and neuropathic and severe pain. The toxin has over 80% success rate for the treatment of pain in humans with a greater potency than morphine. However, Ziconotide causes mast cell degranulation and produces dose-dependent central side effects. These include dizziness, nystagmus, agitation, and dysmetria. There is also orthostatic hypotension in some patients at high doses. It is believed that this may be due to Ziconotide induced mast cell degranulation and/or its effects on the sympathetic ganglion that like the dorsal root ganglion also expresses the N type $Ca^{2+}$ channel. Use-dependent compounds that block preferentially in the higher frequency range>10 Hz should be helpful in minimizing these potential side-effect issues. The firing rate in man of the sympathetic efferents is in the 0.3 Hz range. CNS neurons can fire at high frequencies but generally only do so in short bursts of action potentials. Even with the selectivity imparted by use-dependence intrinsic selectivity against the L type calcium ion channels is still necessary as it is involved in cardiac and vascular smooth muscle contraction.

The third type Cav3 (T-type) channels exist in brain, heart, kidney, liver, etc. They are insensitive to both the dihydropyridines that block Cav1 channels and the spider and cone snail toxins that block the Cav2 channels. T-type $Ca^{2+}$ channels are expected to be novel therapeutic targets for the treatment of various cardiovascular disorders such as heart failure, arrhythmia, hypertension, neuronal disorders such as epilepsy and pain, as well as cancer. Inhibition of T-type $Ca^{2+}$ channels may result in long-term organ protection through improvement of local microcirculation and reduction of adverse hormonal effects. However, there are no widely useful pharmacological agents that block T-type calcium currents. The organic calcium ion channels blocker mibefradil is somewhat selective for T-type versus L-type calcium current and showed strong side effects due to drug interaction at the cytochrome P-450 3A4 enzyme which was unrelated to T-type $Ca^{2+}$ channel blockade. The peptide kurtoxin inhibits the activation gating of Cav3.1 and Cav3.2 channels. Development of more specific and high-affinity blockers of the Cav3 family of calcium ion channels would be useful for therapy and a more detailed analysis of the physiological roles of these channels. The T-type $Ca^{2+}$ channel has properties different from those of the L-type such as more negative voltage range of activation and inactivation, rapid gating kinetics, and resistance to standard $Ca^{2+}$ blockers such as $Ca^{2+}$ channel blockers, which block L-type $Ca^{2+}$ channels.

T-type calcium ion channels have been implicated in pathologies related to various diseases and disorders, including epilepsy, essential tremor, pain, neuropathic pain, schizophrenia, Parkinson's disease, depression, anxiety, sleep disorders, sleep disturbances, psychosis, schizophreniac, cardiac arrhythmia, hypertension, certain types of cancer, diabetes, infertility, sexual dysfunction and cancer (J Neuroscience, 14, 5485 (1994); Drug Future 30(6), 573-580 (2005); EMBO J, 24, 315-324 (2005)).

The known therapeutic regimens for treating such diseases and disorders have numerous problems and a number of side effects. These side effects include various CNS disturbances such as blurred vision, dizziness, nausea, and sedation as well more potentially life threatening cardiac arrhythmias and cardiac failure. Accordingly, a more physiological way, to develop additional $Ca^{2+}$ channel blockers/antagonists, preferably those with higher potency, high selectivity and fewer side effects, to treat these diseases and disorders would be highly desirable.

U.S. Pat. No. 4,342,870 discloses a number of 3-[(1-piperidinyl)alkyl]-4H-pyrido[1,2-a]pyrimidin-4-one derivatives with a specific focus on 3-(2-{4-[(4-fluorophenyl)carbonyl]piperidin-1-yl}ethyl)-2-methyl-4H-pyrido[1,2-a]pyrimidin-4-one (pirenperone) as a serotonin antagonist qualities. It is important to note that U.S. Pat. No. 4,342,870 does not disclose or suggest the use of those derivatives as analgesics.

WO 2005/041971 A1 presents two structural formulas shared a common core structure of "Ar—OCH$_2$F", wherein Ar is a substituted or unsubstituted phenyl or heterophenyl ring, and F is phenyl or heteroaryl. This core structure is marked different from the formulas or compounds of the present application. The compounds disclosed in U.S. Patent Application Publication Nos. 2006/0154929 A1 and U.S. Patent Application Publication No. 2007/0259867 A1 are also markedly different from the formulas or compounds of the present application.

SUMMARY OF THE INVENTION

In one aspect, the present invention provides a method of treating a disease, symptom, or condition associated with T-type calcium ion channels comprising administering a therapeutically effective amount of a compound of formula (I), or the salt, solvate, ester, and/or prodrug thereof, to a patient in need thereof,

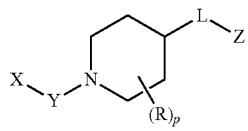

(I)

wherein,

X is a substituted or unsubstituted fused-bicyclic heterocyclyl;

Y is substituted or unsubstituted alkylene;

L is —C(O)—, —C(=S)—, —C(=NR$^1$)—, —C(=N—OR$^1$)—, —S(O)—, —S(O)$_2$—, or —C(R$^2$R$^3$)—;

Z is aryl, substituted aryl, heteroaryl, or substituted heteroaryl;

p is an integer of 0, 1, 2, 3, or 4;

each R is independently halo, alkyl, substituted alkyl, heteroalkyl, substituted heteroalkyl, hydroxyl, alkoxy, amino, alkamino, cyano, or nitro;

R$^1$ is hydrogen, alkyl, or substituted alkyl; and

R$^2$ and R$^3$ are independently hydrogen, halo, alkyl, substituted alkyl, heteroalkyl, substituted heteroalkyl, hydroxyl, alkoxy, amino, alkamino, cyano, or nitro.

In another aspect, the present invention provides a method of modulating T-type calcium ion channels comprising contacting a compound of formula (I), or the salt, solvate, ester, and/or prodrug thereof, with the calcium ion channels.

DETAILED DISCLOSURE OF THE INVENTION

Definitions

Figure 1:
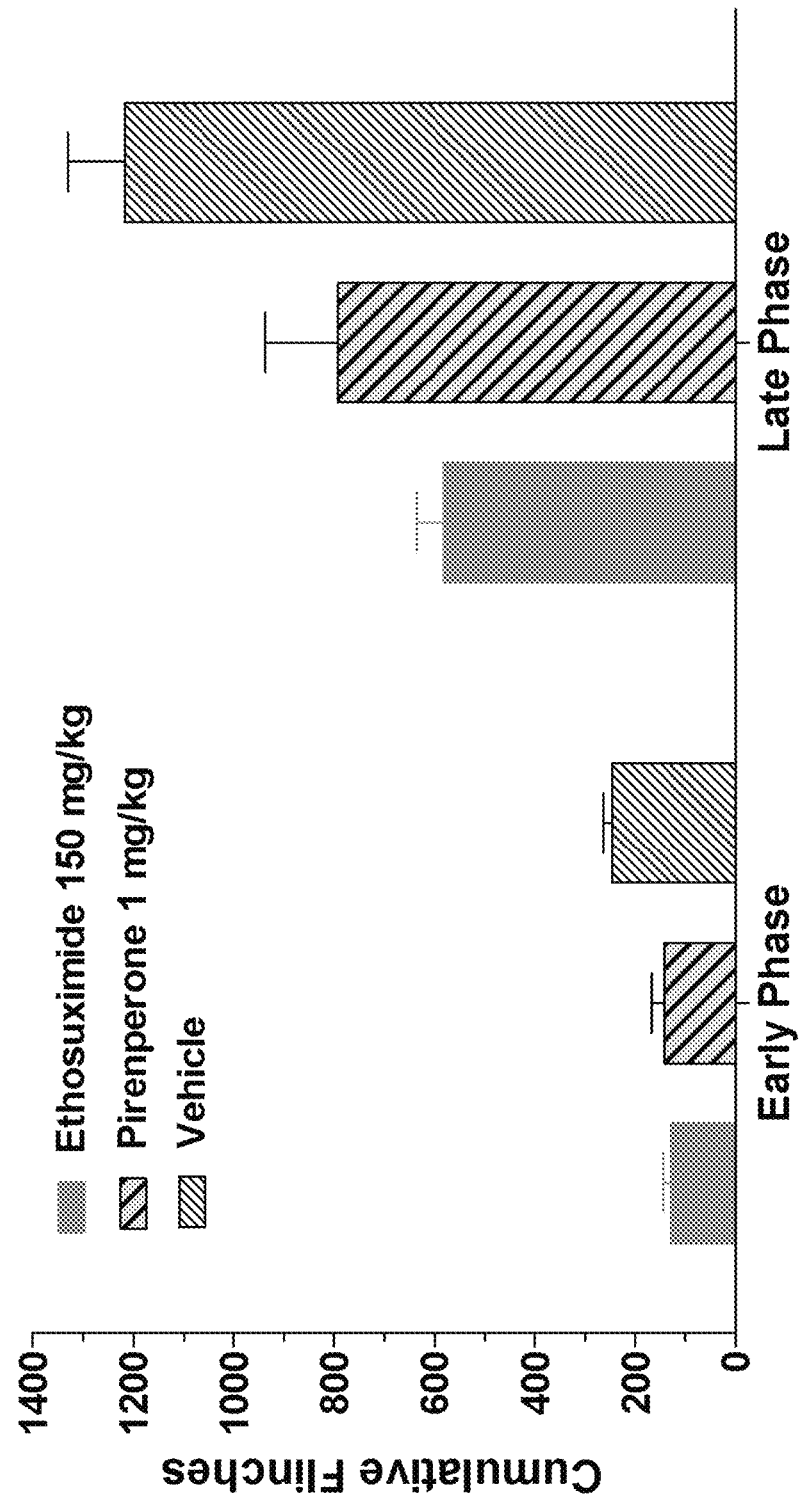
FIG. 1 is a graph showing reduction of Formalin induced pain in rat animal models of hyperalgesia by pirenperone.

"Alkyl" by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms (C$_1$-C$_{20}$ alkyl). In other embodiments, an alkyl group comprises from 1 to 10 carbon atoms (C$_1$-C$_{10}$ alkyl). In still other embodiments, an alkyl group comprises from 1 to 6 carbon atoms (C$_1$-C$_6$ alkyl).

"Alkanyl" by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1- yl, prop-2-yn-1-yl, etc.; butynyls such as but-1-yn-1-yl, but-1-yn-3-yl, but-3-yn-1-yl, etc.; and the like.

"Alkoxy" by itself or as part of another substituent, refers to a radical of the formula —O—R, where R is alkyl or substituted alkyl as defined herein.

"Alkoxycarbonyl" by itself or as part of another substituent, refers to a radical of the formula —C(O)O—R, where R is alkyl or substituted alkyl as defined herein.

"Alkamino" by itself or as part of another substituent refers to a radical —NHR or —NR$_2$, wherein R is alkyl or substituted alkyl.

"Acyl" by itself or as part of another substituent refers to a radical —C(O)R, where R is hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein. Representative examples include, but are not limited to formyl, acetyl, cyclohexylcarbonyl, cyclohexylmethylcarbonyl, benzoyl, benzylcarbonyl and the like.

"Aryl" by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl). In other embodiments, an aryl group comprises from 6 to 15 carbon atoms ($C_6$-$C_{15}$ aryl). In still other embodiments, an aryl group comprises from 6 to 15 carbon atoms ($C_6$-$C_{10}$ aryl).

"Arylalkyl" by itself or as part of another substituent, refers to an acyclic alkyl group in which one of the hydrogen atoms bonded to a carbon atom, typically a terminal or sp$^3$ carbon atom, is replaced with an aryl group as, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) alkyl and the aryl moiety is ($C_6$-$C_{20}$) aryl. In other embodiments, an arylalkyl group is ($C_6$-$C_{20}$) arylalkyl, e.g., the alkanyl, alkenyl or alkynyl moiety of the arylalkyl group is ($C_1$-$C_8$) alkyl and the aryl moiety is ($C_6$-$C_{12}$) aryl. In still other embodiments, an arylalkyl group is ($C_6$-$C_{15}$) arylalkyl, e.g., the alkanyl, alkenyl or alkynyl moiety of the arylalkyl group is ($C_1$-$C_5$) alkyl and the aryl moiety is ($C_6$-$C_{10}$) aryl.

"Aryloxycarbonyl" by itself or as part of another substituent, refers to a radical of the formula —C(O)—O—R, where R is aryl, substituted aryl, arylalkyl, substituted arylalkyl, heteroaryl, substituted heteroaryl, heteroarylalkyl or substituted heteroarylalkyl.

"Cycloalkyl or carbocyclyl" by itself or as part of another substituent, refers to a saturated or unsaturated cyclic alkyl radical, as defined herein. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In some embodiments, the cycloalkyl group comprises from 3 to 10 ring atoms ($C_3$-$C_{10}$ cycloalkyl). In other embodiments, the cycloalkyl group comprises from 3 to 7 ring atoms ($C_3$-$C_7$ cycloalkyl).

"Cycloalkylalkyl" by itself or as part of another substituent, refers to an acyclic alkyl group in which one of the hydrogen atoms bonded to a carbon atom, typically a terminal or sp$^3$ carbon atom, is replaced with an cycloalkyl group as, as defined herein.

"Cycloheteroalkyl or heterocyclyl" by itself or as part of another substituent, refers to a saturated, unsaturated, or partially unsaturated cyclic alkyl radical in which one or more carbon atoms (and optionally any associated hydrogen atoms) are independently replaced with the same or different heteroatom. As used herein, cycloheteroalkyl or heterocyclyl includes heteroaryl. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidone, quinuclidine, and the like. In some embodiments, the cycloheteroalkyl group comprises from 3 to 10 ring atoms (3-10 membered cycloheteroalkyl). In other embodiments, the cycloalkyl group comprise from 5 to 7 ring atoms (5-7 membered cycloheteroalkyl). As used herein, cycloheteroalkyl or heterocyclyl may be monocyclic, bicyclic, or multicyclic. The bicyclic or multicyclic rings may be fused or non-fused.

A cycloheteroalkyl group may be substituted at a heteroatom, for example, a nitrogen atom, with a ($C_1$-$C_6$) alkyl group. As specific examples, N-methyl-imidazolidinyl, N-methyl-morpholinyl, N-methyl-piperazinyl, N-methyl-piperidinyl, N-methyl-pyrazolidinyl and N-methyl-pyrrolidinyl are included within the definition of "cycloheteroalkyl." A cycloheteroalkyl group may be attached to the remainder of the molecule via a ring carbon atom or a ring heteroatom.

"Cycloheteroalkylalkyl" by itself or as part of another substituent, refers to an acyclic alkyl group in which one of the hydrogen atoms bonded to a carbon atom, typically a terminal or sp$^3$ carbon atom, is replaced with a cycloheteroalkyl group as, as defined herein.

"Heteroalkyl", "Heteroalkanyl", "Heteroalkenyl", and "Heteroalkynyl" by themselves or as part of other substituents, refer to alkyl, alkanyl, alkenyl and alkynyl groups, respectively, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, O, S, N, Si, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups include, but are not limited to, —O—, —S—, —O—O—, —S—S—, —O—S—, —NR$_2$—, =N—N=, —N=N—, —N=N—NR$_2$, —PR—, —P(O)$_2$—, —POR—, —O—P(O)$_2$—, —SO—, —SO$_2$—, —SnR$_2$— and the like, where each R is independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or sp³ carbon atom, is replaced with a heteroaryl group. Where specific alkyl moieties are intended, the nomenclature heteroarylalkanyl, heteroarylakenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is $(C_1-C_6)$ alkyl and the heteroaryl moiety is a 5-15-membered heteroaryl. In other embodiments, the heteroarylalkyl is a 6-13 membered heteroarylalkyl, e.g., the alkanyl, alkenyl or alkynyl moiety is $(C_1-C_3)$ alkyl and the heteroaryl moiety is a 5-10 membered heteroaryl.

"Implicated" means culpably involved or causally connected to.

"Modulating" refers to adjusting, varying, or changing. As used herein, modulation of calcium ion channel includes antagonizing, agonizing, or partially antagonizing. That is, the compounds of the present invention may act as antagonists, agonists, or partial antagonists of the calcium ion channel activity.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" refers to a parent aromatic ring system in which one or more carbon atoms (and optionally any associated hydrogen atoms) are each independently replaced with the same or different heteroatom. Typical heteroatoms to replace the carbon atoms include, but are not limited to, N, P, O, S, Si, etc. Specifically included within the definition of "parent heteroaromatic ring system" are fused ring systems in which one or more of the rings are aromatic and one or more of the rings are saturated or unsaturated, such as, for example, benzodioxan, benzofuran, chromane, chromene, indole, indoline, xanthene, etc. Typical parent heteroaromatic ring systems include, but are not limited to, arsindole, carbazole, O-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Patient" includes mammals, such as, for example, humans.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Prodrug or softdrug" refers to a precursor of a pharmaceutically active compound wherein the precursor itself may or may not be pharmaceutically active but, upon administration, will be converted, either metabolically or otherwise, into the pharmaceutically active compound or drug of interest. For example, prodrug or softdrug is an ester or an ether form of a pharmaceutically active compound. Several prodrugs have been prepared and disclosed for a variety of pharmaceuticals. See, for example, Bundgaard, H. and Moss, J., J. Pharm. Sci. 78: 122-126 (1989). Thus, one of ordinary skill in the art knows how to prepare these precursors, prodrugs or softdrugs with commonly employed techniques of organic synthesis.

"Substituted" when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^bR^b)$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s are taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl.

Similarly, substituent groups useful for substituting unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^b C(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, —$R^a$, —$O^-$, —$OR^b$, —$SR^b$, —$S^-$, —$NR^cR^c$, trihalomethyl, —$CF_3$, —CN, —NO, —$NO_2$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups from the above lists useful for substituting other specified groups or atoms will be apparent to those of skill in the art.

The substituents used to substitute a specified group can be further substituted, typically with one or more of the same or different groups selected from the various groups specified above.

"Treating" or "treatment" of any disease or disorder refers, in some embodiments, to ameliorating or preventing the disease or disorder or any symptom/condition associated therewith (i.e., arresting or reducing the development of the disease or at least one of the clinical symptoms thereof). In other embodiments "treating" or "treatment" refers to ameliorating at least one physical parameter, which may not be discernible by the patient. In yet other embodiments, "treating" or "treatment" refers to inhibiting the disease or disorder, either physically, (e.g., stabilization of a discernible symptom), physiologically, (e.g., stabilization of a physical parameter) or both. In yet other embodiments, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, etc., of the patient to be treated.

"Vehicle" refers to a diluent, adjuvant, excipient or carrier with which a compound is administered.

The term "a compound of the present invention", "the compound of the present invention", or "compounds of the present invention" includes one or more compounds covered by the generic formula (I) and/or any subgeneric formula thereof including the racemic mixtures, enantiomers, diastereomers, tautomers, and other isomers thereof.

These compounds and pharmaceutically acceptable compositions are useful for treating or lessening the severity of a variety of diseases, disorders, symptoms, or conditions, including, but not limited to, acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, cancer pain.

T-type calcium ion channels blockers are also useful for the treatment of sleep disorders, mood disorders, depression, migraine headache, neuronal excitability disorders, hypertension, stoke, cardiovascular diseases, hyperaldosteronemia, preterm labor, urinary incontinence, brain aging, or neurodegenerative related diseases such as Alzheimer's disease. See e.g., WO 01/02561; WO 00/02455; JP11035483; and Chemin, J. Physiol., 540, 3-14, (2002). Additionally, T-type calcium ion channels play a role in pancreatic beta-cell insulin secretion. Therefore, T-type blockers may be useful for treatment of hypo- and hyperinsulinemia and the treatment and/or prevention of type 1 and type 2 diabetes as well as microvascular or macrovascular diseases associated with diabetes. See, e.g., Bhattacharjee, Endocrinology, 138, 3735-40, (1997), and WO 00/15845. T-type calcium ion channel blockers may also be useful in the treatment of cancer. See e.g., WO 00/59882 and WO 2001019845.

EMBODIMENTS OF THE PRESENT INVENTION AND THEIR USE

In one aspect, the present invention provides compounds of formula (I), or the salt, solvate, ester, and/or prodrug thereof, to a patient in need thereof,

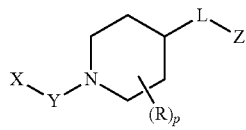

(I)

wherein,

X is a substituted or unsubstituted fused-bicyclic heterocyclyl;

Y is substituted or unsubstituted alkylene;

L is —C(O)—, —C(=S)—, —C(=NR$^1$)—, —C(=N—OR$^1$)—, —S(O)—, —S(O)$_2$—, or C(R$^2$R$^3$)—;

Z is aryl, substituted aryl, heteroaryl, or substituted heteroaryl;

p is an integer of 0, 1, 2, 3, or 4;

each R is independently halo, alkyl, substituted alkyl, heteroalkyl, substituted heteroalkyl, hydroxyl, alkoxy, amino, alkamino, cyano, or nitro;

R$^1$ is hydrogen, alkyl, or substituted alkyl; and

R$^2$ and R$^3$ are independently hydrogen, halo, alkyl, substituted alkyl, heteroalkyl, substituted heteroalkyl, hydroxyl, alkoxy, amino, alkamino, cyano, or nitro.

In one embodiment of formula (I), —C(R$^2$R$^3$)— is —CHOH—. That is, L is —CHOH—.

In certain embodiments of the present invention, the compound of formula (I) has a structural formula selected from the group consisting of formula (II), or the salt, solvate, ester, and/or prodrug thereof, to a patient in need thereof, (II)

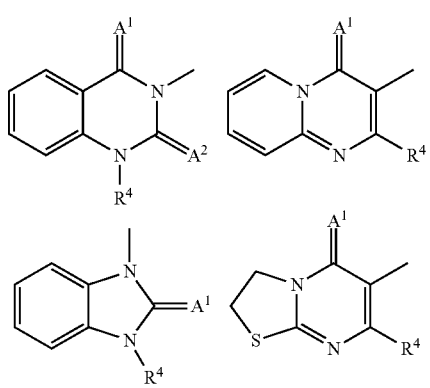

wherein X is a substituted or unsubstituted fused-bicyclic heterocyclyl, selected from the group consisting of:

mm is an integer of 1, 2, 3, or 4;

nn is an integer of 0, 1, 2, 3, 4, or 5;

L is —C(O)—, —C(=S)—, or —CHOH—;

each R$^4$ is independently hydrogen, alkyl, substituted alkyl, heteroalkyl, substituted heteroalkyl, hydroxyl, alkoxy, amino, or alkamino; and each R$^5$ is independently halo, alkyl, substituted alkyl, heteroalkyl, substituted heteroalkyl, hydroxyl, alkoxy, amino, alkamino, cyano, or nitro.

In certain embodiments of the present invention, the compound of formula (II) has a structural formula selected from the group consisting of formula (Ia), formula (Ib), formula (Ic), and formula (Ic), or the salt, solvate, ester, and/or prodrug thereof,

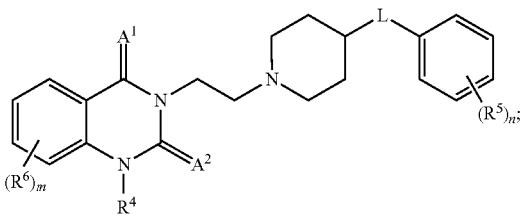

(Ia)

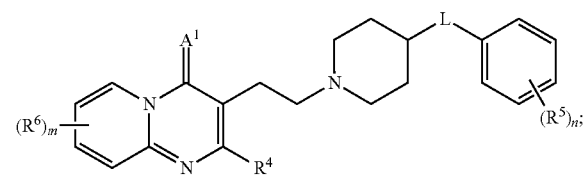

(Ib)

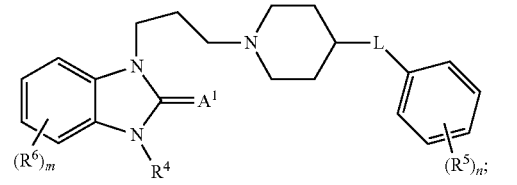

(Ic)

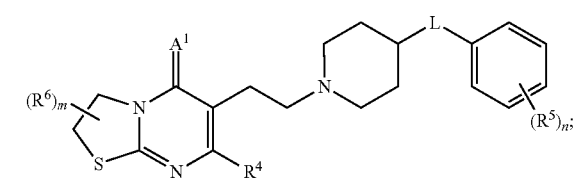

(Id)

wherein each A$^1$ and A$^2$ is independently O, S, —NR, or —N—OR;

each R$^4$ is independently hydrogen, alkyl, substituted alkyl, heteroalkyl, substituted heteroalkyl, hydroxyl, alkoxy, amino, or alkamino;

each L is independently —C(O)—, —C(=S)—, or —CHOH—;

each R$^5$ and R$^6$ are independently halo, alkyl, substituted alkyl, heteroalkyl, substituted heteroalkyl, hydroxyl, alkoxy, amino, alkamino, cyano, or nitro;

each n is independently an integer of 0, 1, 2, 3, 4, or 5; and each m is independently an integer of 0, 1, 2, 3, or 4.

In some specific embodiments, the present invention provides compounds selected from the group consisting of 1
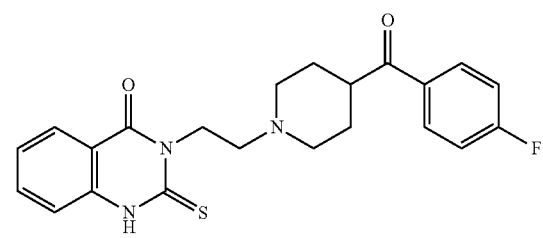
(altanserin)
2
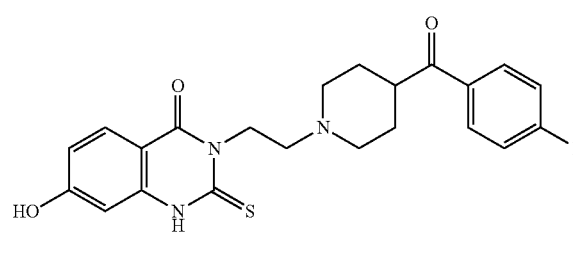
3
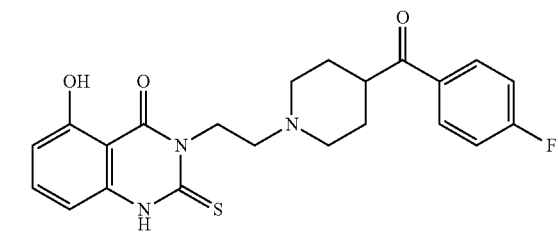
5
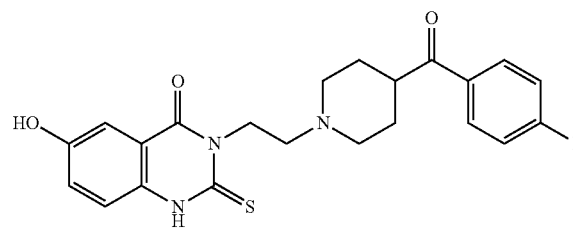
7
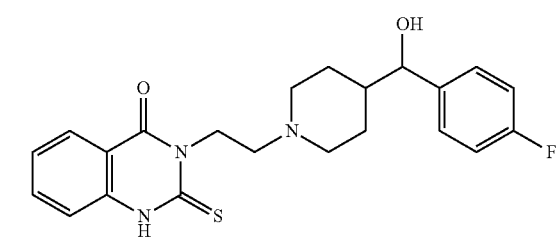
8
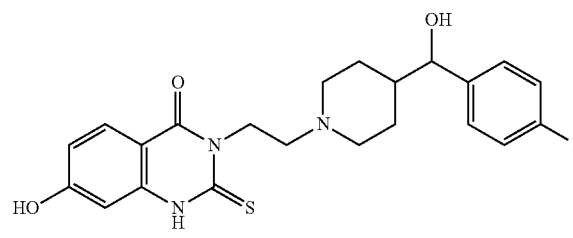
10
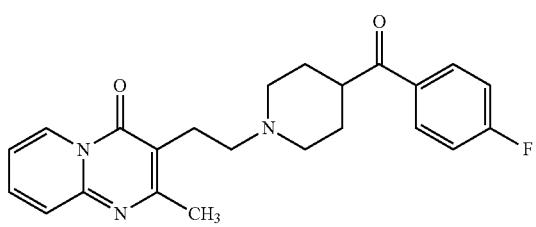
(pirenperone)
11
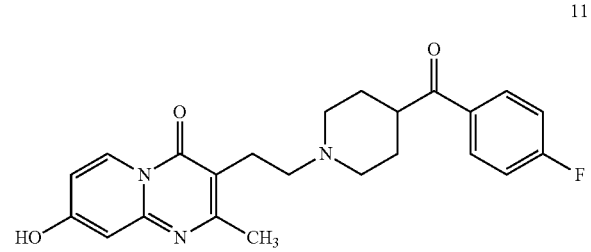
13
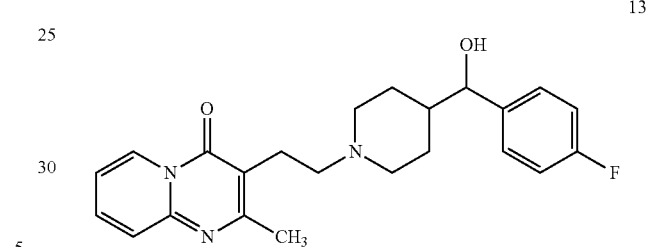
15
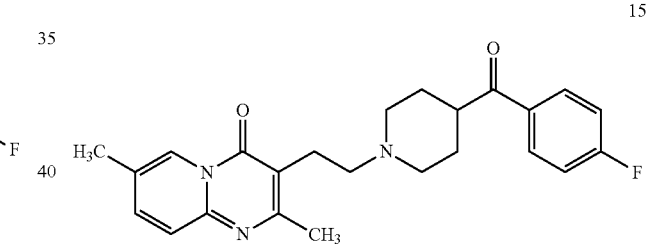
(metrenperone)
16
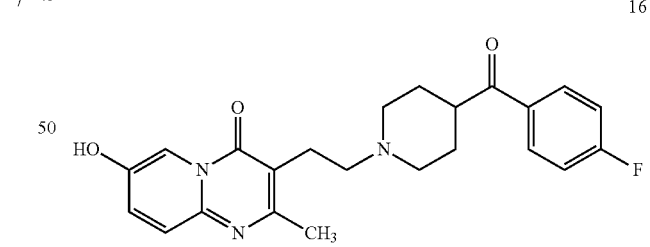
18
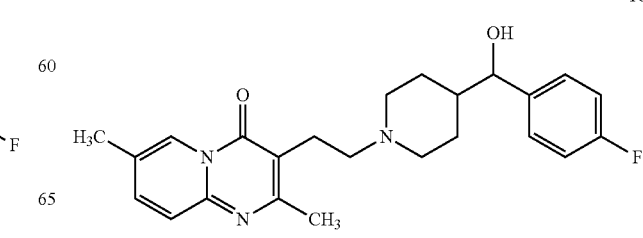

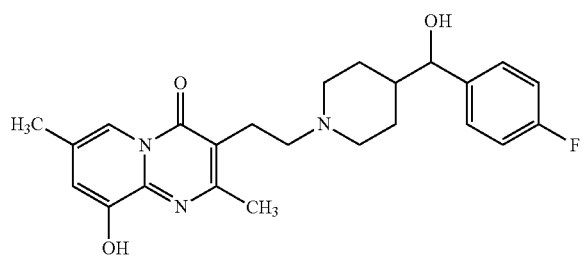

20

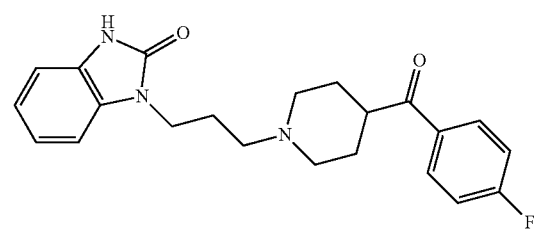

22

(declenperone)

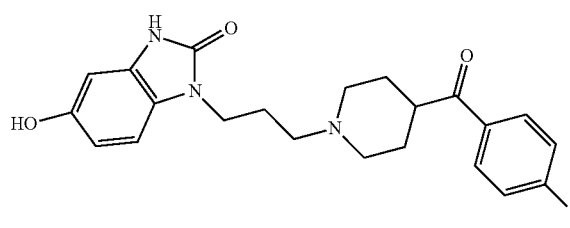

24

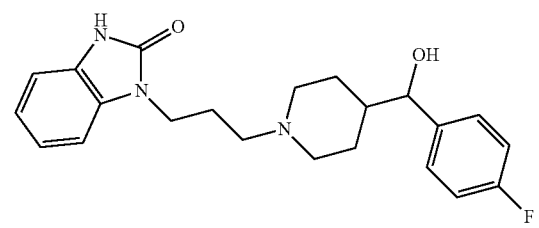

26

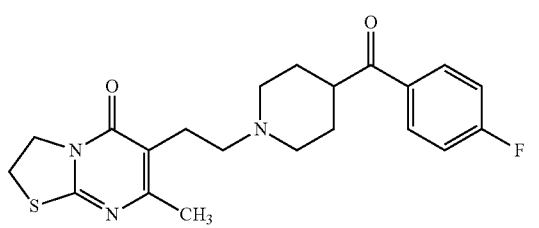

(setoperone)

28

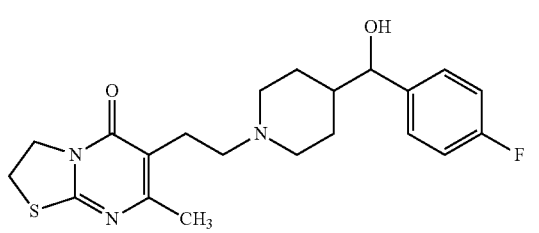

29

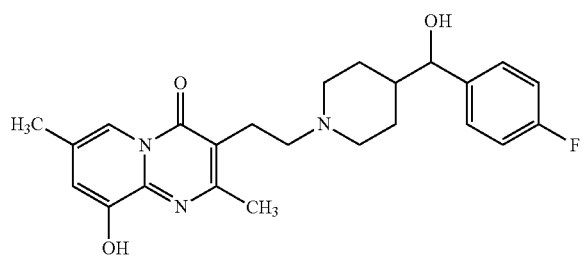

30

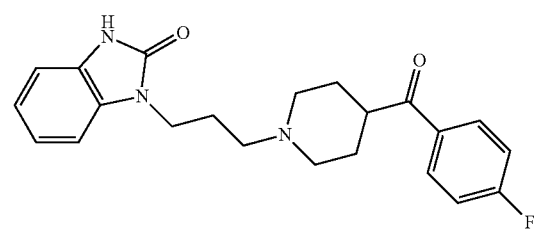

32 including the racemic mixtures, enantiomers, diastereomers, tautomers, and other isomers; or the salt, solvate, ester, and/or prodrug thereof.

The above-listed compounds may also be represented by their chemical names as follows:

ID IUPAC Name
1 3-(2-{4-[(4-fluorophenyl)carbonyl]piperidin-1-yl}ethyl)-2-thioxo-2,3-dihydroquinazolin-4(1H)-one (altanserin)
2 3-(2-{4-[(4-fluorophenyl)carbonyl]piperidin-1-yl}ethyl)-7-hydroxy-2-thioxo-2,3-dihydroquinazolin-4(1H)-one
3 3-(2-{4-[(4-fluorophenyl)carbonyl]piperidin-1-yl}ethyl)-5-hydroxy-2-thioxo-2,3-dihydroquinazolin-4(1H)-one
5 3-(2-{4-[(4-fluorophenyl)carbonyl]piperidin-1-yl}ethyl)-6-hydroxy-2-thioxo-2,3-dihydroquinazolin-4(1H)-one
7 3-(2-{4-[(R/S)-(4-fluorophenyl)(hydroxy)methyl]piperidin-1-yl}ethyl)-2-thioxo-2,3-dihydroquinazolin-4(1H)-one
8 3-(2-{4-[(R/S)-((4-fluorophenyl)(hydroxy)methyl]piperidin-1-yl}ethyl)-7-hydroxy-2-thioxo-2,3-dihydroquinazolin-4(1H)-one
10 3-(2-{4-[(4-fluorophenyl)carbonyl]piperidin-1-yl}ethyl)-2-methyl-4H-pyrido[1,2-a]pyrimidin-4-one (pirenperone)
11 3-(2-{4-[(4-fluorophenyl)carbonyl]piperidin-1-yl}ethyl)-8-hydroxy-2-methyl-4H-pyrido[1,2-a]pyrimidin-4-one
13 3-(2-{4-[(R/S)-(4-fluorophenyl)(hydroxy)methyl]piperidin-1-yl}ethyl)-2-methyl-4H-pyrido[1,2-a]pyrimidin-4-one
15 3-(2-{4-[(4-fluorophenyl)carbonyl]piperidin-1-yl}ethyl)-2,7-dimethyl-4H-pyrido[1,2-a]pyrimidin-4-one (metrenperone)
16 3-(2-{4-[(4-fluorophenyl)carbonyl]piperidin-1-yl}ethyl)-7-hydroxy-2-methyl-4H-pyrido[1,2-a]pyrimidin-4-one
18 3-(2-{4-[(R/S)-(4-fluorophenyl)(hydroxy)methyl]piperidin-1-yl)}ethyl)-2,7-dimethyl-4H-pyrido[1,2-a]pyrimidin-4-one
20 3-(2-{4-[(R/S)-(4-fluorophenyl)(hydroxy)methyl]piperidin-1-yl}ethyl)-9-hydroxy-2,7-dimethyl-4H-pyrido[1,2-a]pyrimidin-4-one
22 1-(3-{4-[(4-fluorophenyl)carbonyl]piperidin-1-yl}propyl)-1,3-dihydro-2H-benzimidazol-2-one (declenperone)
24 1-(3-{4-[(4-fluorophenyl)carbonyl]piperidin-1-yl}propyl)-5-hydroxy-1,3-dihydro-2H-benzimidazol-2-one 26 1-(3-{4-[(R/S)-(4-fluorophenyl)(hydroxy)methyl]piperidin-1-yl}propyl)-1,3-dihydro-2H-benzimidazol-2-one
28 6-(2-{4-[(4-fluorophenyl)carbonyl]piperidin-1-yl}ethyl)-7-methyl-2,3-dihydro-5H-[1,3]thiazolo[3,2-a]pyrimidin-5-one (setoperone)
29 6-(2-{4-[(R/S)-(4-fluorophenyl)(hydroxy)methyl]piperidin-1-yl}ethyl)-7-methyl-2,3-dihydro-5H-[1,3]thiazolo[3,2-a]pyrimidin-5-one
30 (2R/S)-6-(2-{4-[(4-fluorophenyl)carbonyl]piperidin-1-yl}ethyl)-2-hydroxy-7-methyl-2,3-dihydro-5H-[1,3]thiazolo[3,2-a]pyrimidin-5-one
32 (2R/S)-6-(2-{4-[(R/S)-(4-fluorophenyl)(hydroxy)methyl]piperidin-1-yl}ethyl)-2-hydroxy-7-methyl-2,3-dihydro-5H-[1,3]thiazolo[3,2-a]pyrimidin-5-one The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

The present compounds and a pharmaceutical compositions thereof are useful for treating or lessening the severity of a variety of diseases, disorders, symptoms, or conditions, including, but not limited to, acute pain, chronic pain, neuropathic pain, inflammatory pain, radicular pain, sciatica, back pain, head pain, neck pain, severe or intractable pain, post-surgical pain, visceral pain, cancer pain, osteoarthritis pain, peripheral neuropathy, nociceptive pain, breakthrough pain, migraine, angina, tonic pain, persistent pain, postoperative pain, chemical-induced pain, chemotherapy-induced pain, drug-induced pain, a generalized pain disorder, skeletal muscle spasms, convulsive seizures, cancer, or a combination thereof.

The present compounds and pharmaceutical compositions thereof are also useful for the treatment of any disease, symptom, or condition that is due to causalgia, diabetes, collagen vascular disease, trigeminal neuralgia, spinal cord injury, brain stem injury, thalamic pain syndrome, complex regional pain syndrome type I/reflex sympathetic dystrophy, Fabry's syndrome, small fiber neuropathy, cancer, cancer chemotherapy, chronic alcoholism, stroke, abscess, demyelinating disease, viral infection, anti-viral therapy, AIDS, AIDS therapy, burn, sunburn, arthritis, colitis, carditis, dermatitis, myositis, neuritis, mucositis, urethritis, cystitis, gastritis, pneumonitis, collagen vascular disease, trauma, surgery, amputation, toxin, chemotherapy, fibromyalgia, irritable bowel syndrome, a temporomandibular disorder, vascular disease, arteriosclerosis, sleep disorders, metabolic disorders, gastrointestinal disease, prostate tumor or cancer, schizophrenia, drug dependence, tinnitus, dementia, asthma, cluster headaches, trigeminal neuralgia, herpetic neuralgia, general neuralgias, epilepsy, neurodegenerative disorders, arthritis, anxiety, depression, myotonia, arrythmia, movement disorders, neuroendocrine disorders, ataxia, multiple sclerosis, irritable bowel syndrome, incontinence, postherpetic neuralgia, diabetic neuropathy, cancer, contraception, nervous system injury, seizure, convulsion, Huntington's chorea, Alzheimer' disease, autoimmune disease, tremor, retinopathy, neoplasm, inflammation, cranial neuropathy, type 1 or type 2 diabetes, hyperaldosteronemia, preterm labor, urinary incontinence, brain aging, or a combination thereof.

The subject compounds are useful in a method of modulating calcium, particularly T-type calcium ion channels activity in a patient such as a mammal in need of such modulation comprising the administration of an effective amount of the compound. Preferably, the modulation includes antagonizing or inhibiting. The present invention is directed to the use of the compounds disclosed herein as antagonists of calcium, particularly T-type calcium ion channels activity. In addition to primates, especially humans, a variety of other mammals can be treated according to the method of the present invention.

The present invention is further directed to a method for the manufacture of a medicament for modulating calcium, particularly T-type calcium ion channels activity or treating the disorders and diseases noted herein in humans and animals.

The subject treated in the present methods is generally a mammal, preferably a human being, male or female. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder. The terms "administration of" and or "administering" a compound should be understood to mean providing a compound of the invention or a prodrug or a softdrug of a compound of the invention to the individual in need thereof.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention, or a salt, solvate, and/or prodrug thereof, and a pharmaceutically acceptable carrier or vehicle. By "pharmaceutically acceptable" it is meant the carrier, diluent or excipient must be compatible with the other ingredients of the formulation and not deleterious to the recipient thereof. In one embodiment, the compound of the present invention, or a salt, solvate, and/or prodrug thereof, in the present pharmaceutical composition does not include a compound having structural formula (Ia), nor a salt, solvate, and/or prodrug thereof. In one embodiment, the compound of the present invention, or a salt, solvate, and/or prodrug thereof, in the present pharmaceutical composition is the only active ingredient in the pharmaceutical composition for the intended therapeutic purpose.

The utility of the compounds in accordance with the present invention as calcium, particularly T-type calcium ion channel antagonists may be readily determined without undue experimentation by methodology well known in the art, including in (I) freshly dissociated neurons from dorsal root ganglia (DRG) or thalamus of adult rats or mouse to study pharmacological properties of low-voltage-activated T-type $Ca^{2+}$ current after the inhibition of other ion channels in native DRG or thalamus cells by utilizing the cell patch-clamp method [described, for examples, by S. M. Todorovic and C. J. Lingle, The Journal of Neurophysiology, Vol. 79 No. 1 Jan. 1998, pp. 240-252, and Joksovic, et al, *J Physiol* 574.2 pp 415-430 (2006)]; (II) the "FLIPR $Ca^{2+}$ Flux Assay" and (III) the "T-type Calcium ($Ca^{2+}$) Antagonists Voltage-Clamp Assay" [described by Xia, et al., Assay and Drug Development Tech., 1(5), 637-645 (2003)]. In a typical experiment ion channel function from HEK 293 cells expressing the calcium or T-type calcium ion channel alpha-1G, H, or I (Cav3.1, Cav3.2, Cav3.3) is recorded to determine the activity of compounds in blocking the calcium current mediated by the calcium or T-type calcium ion channel alpha-1G, H, or I (Cav3.1, Cav3.2, Cav3.3). In this T-type calcium (C2+) ion channels antagonist voltage-clamp assay calcium currents are elicited from the resting state of the human alpha-1G, H, or I (Cav3.1, Cav3.2, Cav3.3) calcium ion channel as follows. Sequence information for T-type (Low-voltage activated) calcium ion channels are fully disclosed in e.g., U.S. Pat. Nos. 5,618,720, 5,686,241, 5,710,250, 5,726,035, 5,792,846, 5,846,757, 5,851,824, 5,874,236, 5,876,958, 6,013,474, 6,057,114, 6,096,514, WO99/28342, and J. Neuroscience, 19(6):1912-1921 (1999). Cells expressing the T-type channels were grown in growth media which comprised: DMEM, 10% Tetsystem approved FBS (Clontech Laboratories Inc.), 100 microgram/ml Penicillin/Streptomycin, 2 mM L-Glutamine, 150 microgram/ml Zeocin, 5 microgram/ml Blasticidin. T-channel expression was induced by exposing the cells to 2 mM Tetracycline for 24 hrs. Glass pipettes are pulled to a tip diameter of 1-2 micrometer on a pipette puller. The pipettes are filled with the intracellular solution and a chloridized silver wire is inserted along its length, which is then connected to the headstage of the voltage-clamp amplifier. Trypsinization buffer was 0.05% Trypsin, 0.53 mM EDTA. The extracellular recording solution consists of (mM): 130 mM NaCl, 4 mM KCl, 1 mM $MgCl_2$, 2 mM $CaCl_2$, 20 roM HEPES, 30 Glucose, pH 7.4. The internal solution consists of (mM): 125 CsCl, 10 TEA-Cl, 10 HEPES, 8 NaCl, 0.06 $CaCl_2$, 0.6 EGTA, 4 ATP-Mg, 0.3 GTP; 135 roM $CsMeSO_3$, 1 $MgCl_2$, 10 CsCl, 5 EGTA, 10 HEPES, pH 7.4; or 135 mM CsCl, 2 $MgCl_2$, 3 MgATP, 2 $Na_2ATP$, 1 Na2GTP, 5 EGTA, 10 HEPES, pH 7.4. Upon insertion of the pipette tip into the bath, the series resistance is noted (acceptable range is between 1-4 megaohm). The junction potential between the pipette and bath solutions is zeroed on the amplifier. The cell is then patched, the patch broken, and, after compensation for series resistance (>=80%), the voltage protocol is applied while recording the whole cell $Ca^{2+}$ current response. Voltage protocols: (1) −80 mV holding potential every 20 seconds pulse to −20 mV for 70 msec duration; the effectiveness of the drug in inhibiting the current mediated by the channel is measured directly from measuring the reduction in peak current amplitude initiated by the voltage shift from −80 mV to −20 mV; (2). −100 mV holding potential every 15 seconds pulse to −20 mV for 70 msec duration; the effectiveness of the drug in inhibiting the current mediated by the channel is measured directly from measuring the reduction in peak current amplitude initiated by the shift in potential from −100 m V to −20 m V. The difference in block at the two holding potentials was used to determine the effect of drug at differing levels of inactivation induced by the level of resting state potential of the cells. After obtaining control baseline calcium currents, extracellular solutions containing increasing concentrations of a test compound are washed on. Once steady state inhibition at a given compound concentration is reached, a higher concentration of compound is applied. % inhibition of the peak inward control $Ca^{2+}$ current during the depolarizing step to −20 mV is plotted as a function of compound concentration.

The intrinsic T-type calcium ion channel antagonist activity of a compound which may be used in the present invention may be determined by these assays. In particular, the compounds of the aforementioned examples had activity in antagonizing the T-type calcium ion channels in the aforementioned assays, generally with an $IC_{50}$ of less than about 25 µM. Preferred compounds within the present invention had activity in antagonizing the T-type calcium ion channel in the aforementioned assays with an $IC_{50}$ of less than about 1 µM. Such a result is indicative of the intrinsic activity of the compounds in use as antagonists of T-type calcium ion channels activity.

T-type calcium ion channels have been implicated in a wide range of biological functions. This has suggested a potential role for these receptors in a variety of disease processes in humans or other species. The compounds of the present invention have utility in treating, preventing, ameliorating, controlling or reducing the risk of a variety of neurological and psychiatric disorders associated with calcium ion channels, including one or more of the following symptoms, conditions, and/or diseases: movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, seizure disorders, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); heart disease, abnormal heart rhythms and arrythmias, myocardial infarction, congestive heart failure, coronary heart disease, sudden death, stroke, sexual and reproductive dysfunction, such as impaired fertility, infertility, diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function; enhancing memory; increasing memory retention; increasing trained performance; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; sleep disorders, sleep disturbances, including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent waking during sleep; decreasing nocturnal arousals; decreasing the time spent awake following the initial onset of sleep; increasing the total amount of sleep; reducing, the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing the amount of Delta sleep early in the sleep cycle, increasing REM sleep late in the sleep cycle; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia, hypersomnia, idiopathic hypersomnia, repeatability hypersomnia, intrinsic hypersomnia, narcolepsy, interrupted sleep, sleep apnea, obstructive sleep apnea, wakefulness, nocturnal myoclonus, REM sleep interruptions, jet-lag, shift workers' sleep disturbances, dyssonmias, night terror, insomnias associated with depression, emotional/mood disorders, Alzheimer's disease or cognitive impairment, as well as sleep walking and enmesis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; fibromyalgia; syndromes which are manifested by non-restorative sleep and muscle pain or sleep apnea which IS associated with respiratory disturbances during sleep; conditions which result from a diminished quality of sleep; mood disorders, such as depression or more particularly depressive disorders, for example, single episodic or recurrent major depressive disorders and dysthymic disorders, or bipolar disorders, for example, bipolar I disorder, bipolar n disorder and cyclothymic disorder, mood disorders due to a general medical condition, and substance-induced mood disorders; anxiety disorders including acute stress disorder, agomphobia, genemlized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, *cannabis*, cocaine, hallucinogens, inhalants, nicotine, opioids, phencyclidine, sedatives, hypnotics or anxiolytics); attention deficit/hyperactivity disorder (ADHD); conduct disorder; migraine (including migraine headache); urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss;

tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache.

Thus, in preferred embodiments the present invention provides methods for: treating, controlling, ameliorating or reducing the risk of epilepsy, including absence epilepsy; treating or controlling Parkinson's disease; treating essential tremor; treating or controlling pain, including neuropathic pain; enhancing the quality of sleep; augmenting sleep maintenance; increasing REM sleep; increasing slow wave sleep; decreasing fragmentation of sleep patterns; treating insomnia; enhancing cognition; increasing memory retention; treating or controlling depression; treating or controlling psychosis; or treating, controlling, ameliorating or reducing the risk of schizophrenia, in a mammalian patient in need thereof which comprises administering to the patient a therapeutically effective amount of the compound of the present invention.

The compounds of the present invention are further useful in a method for the prevention, treatment, control, amelioration, or reduction of risk of the diseases, disorders, symptoms, and conditions noted herein.

The dosage of active ingredient in the compositions of this invention may be varied. However, it is necessary that the amount of the active ingredient be such that a suitable dosage form is obtained. For example, the present compounds can be incorporated into an oral dose, or an injection, or a transdermal patch or implantation of a depot formulation. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.0001 to 10 mg/kg of body weight daily are administered to the patient, e.g., humans and elderly humans, to obtain effective antagonism of calcium, particularly T-type calcium ion channels. The dosage range will generally be about 0.5 mg to 1.0 g per patient per day which may be administered in single or multiple doses. Preferably, the dosage range will be about 0.5 mg to 500 mg per patient per day; more preferably about 0.5 mg to 200 mg per patient per day; and even more preferably about 5 mg to 50 mg per patient per day. Pharmaceutical compositions of the present invention may be provided in a solid dosage formulation preferably comprising about 0.5 mg to 500 mg active ingredient, more preferably comprising about 1 mg to 250 mg active ingredient. The pharmaceutical composition is preferably provided in a solid dosage formulation comprising about 1 mg, 5 mg, 10 mg, 25 mg, 50 mg, 100 mg, 200 mg or 250 mg active ingredient. For oral administration, the compositions are preferably provided in the form of tablets containing 1.0 to 1000 milligrams of the active ingredient, particularly 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, preferably once or twice per day.

The compounds of the present invention may be co-administered with an additional active agent, i.e., at least one additional active agent. That is, the compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is preferred. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

In one embodiment, the present invention provides a pharmaceutical composition comprising (a) a compound having a structural formula (I), or a salt, solvate, and/or prodrug thereof, as described herein, and (b) an analgesic agent that acts by a mechanism different from a T-type calcium ion channels antagonist. In another embodiment, the present invention provides a pharmaceutical composition, comprising (a) a compound having a structural formula (I), or a salt, solvate, and/or prodrug thereof, as defined herein, and (b) an additional active agent selected from the group consisting of an inhibitor of protein kinase A (PKA), an inhibitor of protein kinase C, an inhibitor of protein kinase C epsilon, an inhibitor of cAMP signaling, a nonsteroidal antiinflammatory drug, a prostaglandin synthesis inhibitor, a local anesthetic, an anticonvulsant, an antidepressant, an opioid receptor agonist, a neuroleptic, a agonist of a $GABA_A$ receptor and a combination thereof.

In one embodiment, the present invention provides a kit comprising (a) a pharmaceutical composition comprising a compound having a structural formula (I), or a salt, solvate, and/or prodrug thereof, as described herein; and (b) instructions for carrying out the combo method as described herein. In another embodiment, the present invention provides a kit comprising (a) a pharmaceutical composition comprising (a1) a compound having a structural formula (I), or a salt, solvate, and/or prodrug thereof, and (a2) at least one additional active agent; and (b) instructions for carrying out the combo therapy as described herein.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be employed in combination with an anti-seizure agent such as carbamazepine, clonazepam, divalproex, ethosuximide, felbamate, fosphenytoin, gabapentin, lamotrigine, levetiracetam, lorazepam, midazolam, oxcarbazepine, phenobarbital, phenytoin, primidone, tiagabine, topiramate, valproate, vigabalrin or zonisamide. In another embodiment, the subject compound may be employed in combination with acetophenazine, alentemol, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene, trifluoperazine or valproic acid.

In another embodiment, the compounds of the present invention may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the compounds of the present invention may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form.

In another embodiment, the compounds of the present invention may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antimflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, car beta pentane, or dextramethorphan; a diuretic; and a sedating or non-sedating antihistamine. In another embodiment, the subject compound may be employed in combination with an L-type calcium channel antagonist, such as amlodipine.

In another embodiment, the compounds of the present invention may be administered in combination with compounds which are known in the art to be useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, other T-type calcium ion channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, etchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perla pine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the compounds of the present invention may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, a-adrenoreceptor antagonists, neurokinin-1 receptor antagonists, atypical anti-depressants, benzodiazepines, 5-HT-1A agonists or antagonists, especially 5-HT-1A partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and seriraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the compounds of the present invention may be employed in combination with anti-Alzheimer's agents; beta-secretase inhibitors; gamma-secretase inhibitors; growth hormone secretagogues; recombinant growth hormone; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine H3 antagonists; AMP A agonists; PDE4 inhibitors; $GABA_A$ inverse agonists; or neuronal nicotinic agonists.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; Bn: benzyl; BuLi: butyllithium; Piv: pivaloyl; Ac: acetyl; THF: tetrahydrofuran; DMSO: dimethylsulfoxide; EDC: N-(3-Dimethylaminopropyl)-N'-ethylcarbodiimide; Boc: tert-butyloxy carbonyl; Et3N: triethylamine; DCM: dichloromethane; DCE: dichloroethane; DME: dimethoxyethane; DBA: diethylamine; DAST: diethylaminosulfur trifluoride; EtMgBr: ethylamgnesium bromide; BSA: bovine serum albumin; TF A: trifluoracetic acid; DMF: N,N-dimethylformamide; $SOCl_2$: thionyl chloride; CDI: carbonyl diimidazole; rt: room temperature; HPLC: high performance liquid chromatography. The compounds of the present invention can be prepared in a variety of fashions.

The compounds of the invention comprise Formula I, as described above can be obtained from commercial sources, such as Aldrich Chemical Co. (Milwaukee, Wis.), Sigma Chemical Co. (St. Louis, Mo.), Maybridge (Cornwall, England), Asinex (Winston-Salem, N.C.), ChemBridge (San Diego, Calif.), ChemDiv (San Diego, Calif.), SPECS (Delft, The Netherlands), Timtec (Newark, Del.) or the compounds can be synthesized. The compounds of the present invention, and other related compounds having different substituents identified by any of the methods described above can be synthesized using techniques and materials known to those of skill in the art, such as described, for example, in March, ADVANCED ORGANIC CHEMISTRY 4.sup.th Ed., (Wiley 1992); Carey and Sundberg, ADVANCED ORGANIC CHEMISTRY 3.sup.rd Ed., Vols. A and B (Plenum 1992), and Green and Wuts, PROTECTIVE GROUPS IN ORGANIC SYNTHESIS 2.sup.nd Ed. (Wiley 1991). Starting materials useful for preparing compounds of the invention and intermediates thereof are commercially available or can be prepared by well-known synthetic methods (see, e.g., Harrison et al., "Compendium of Synthetic Organic Methods", Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-21, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," 3d Edition, John Wiley & Sons, 1995). Other methods for synthesis of the compounds described herein and/or starting materials are either described in the art or will be readily apparent to the skilled artisan. Alternatives to the reagents and/or protecting groups may be found in the references provided above and in other compendiums well known to the skilled artisan. Guidance for selecting suitable protecting groups can be found, for example, in Greene & Wuts, "Protective Groups in Organic Synthesis," Wiley Interscience, 1999. Accordingly, the synthetic methods and strategy presented herein are illustrative rather than comprehensive.

The procedures described herein for synthesizing the compounds of the invention may include one or more steps of protection and deprotection (e.g., the formation and removal of acetal groups). In addition, the synthetic procedures disclosed below can include various purifications, such as column chromatography, flash chromatography, thin-layer chromatography (TLC), recrystallization, distillation, high-pressure liquid chromatography (HPLC) and the like. Also, various techniques well known in the chemical arts for the identification and quantification of chemical reaction products, such as proton and carbon-13 nuclear magnetic resonance ($^1$H and $^{13}$C NMR), infrared and ultraviolet spectroscopy (IR and UV), X-ray crystallography, elemental analysis (EA), HPLC and mass spectroscopy (MS) can be used as well. Methods of protection and deprotection, purification and identification and quantification are well known in the chemical arts.

An example of reduction of Formalin induced pain in rat animal models of hyperalgesia by 3-(2-{4-[(4-fluorophenyl) carbonyl]piperidin-1-yl}ethyl)-2-methyl-4H-pyrido[1,2-a] pyrimidin-4-one (pirenperone) is given in FIG. 1.

Rat Formalin Paw Test (in Vivo Assay): Compounds were assessed for their ability to inhibit the behavioral response evoked by an injection of formalin (50 µl of 5% formalin). A metal band was affixed to the left hind paw of male Holtzman rats (225-250 g, Harlan Industries, Indianapolis Ind.) and each rat was conditioned to the band for 60 min within a plastic cylinder (15 cm diameter). Rats were dosed with either vehicle, positive control compound or a test compound either before (local) or after (systemic) formalin challenge. For local administration, compounds were prepared in either a 1:1.5 vehicle of saline (in mL) and (D)- or (L)-Tartaric acid (in mg), or a 1:1:6 vehicle of DMA (N,N-Dimethylacetamide), Tween 80 and saline, and injected intraperitoneally into the dorsal surface of the right hind paw of the rat 60 min prior to formalin. The number of flinches was counted continuously for 60 min using an automated nociception analyzer (UCSD Anesthesiology Research, San Diego, Calif.). Statistical significance was determined by comparing the total flinches detected in the early (0-10 min, Phase I) and late (11-60 min) phase with an unpaired t-test. Here the antiepileptic drug Ethosiximide, a known T-type calcium ion channels antagonist used an analgesic (WO-2006122035, Gogas. K. R., et al. "Effects of the T-type calcium channel blocker, Elhosuximide. in rodent models of acute and chronic pain", Abstract. IASP 10th World Congress on Pain. San Diego. Calif. 2002) was used as a positive control compound.

Figure 2:
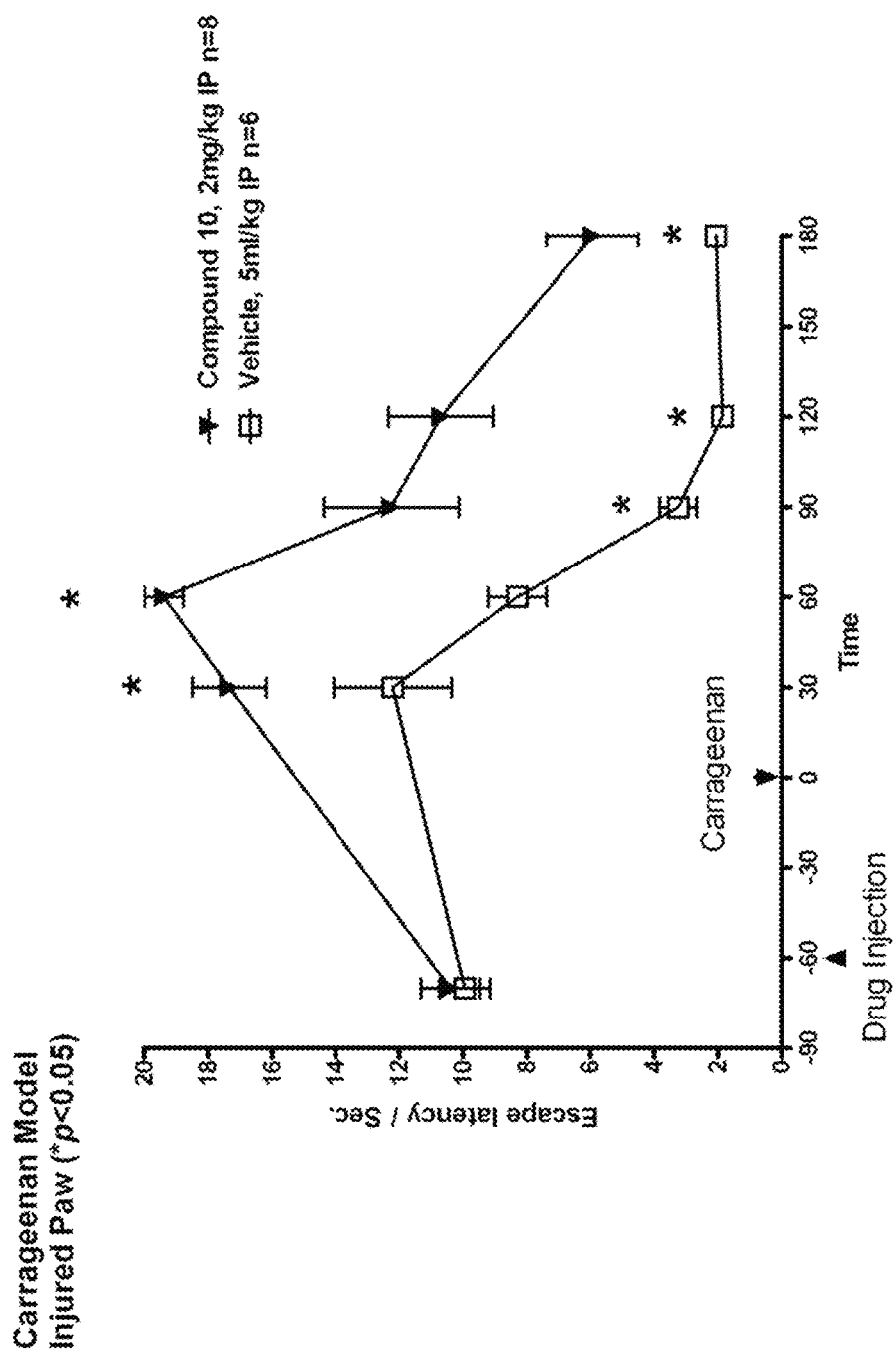
FIG. 2 and FIG. 3 are graphs showing reduction of Carrageenan-induced pain in rat animal model of hyperalgesia by pirenperone.
Figure 3:
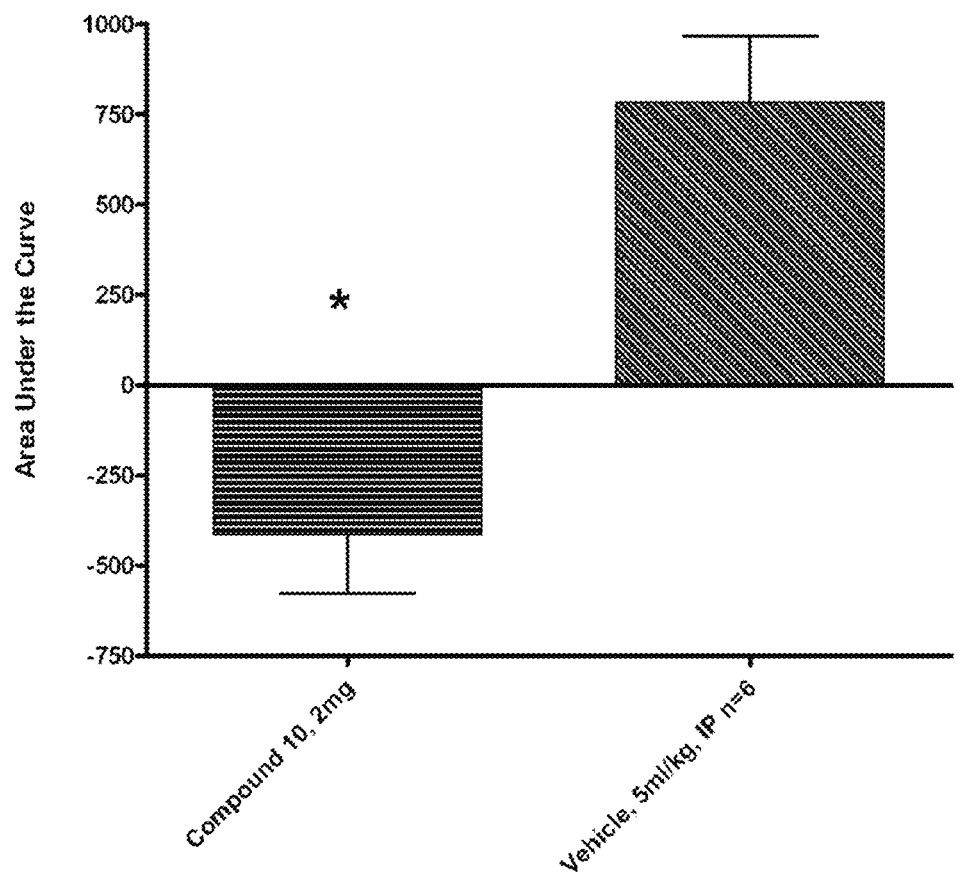

An example of reduction of Carrageenan-induced pain in rat animal model of hyperalgesia by Compound 10 (pirenperone) is given in FIG. 2 and FIG. 3.

INCORPORATION BY REFERENCE

The content of the articles, publications, and patents cited hereinabove are all incorporated by reference in their entirety for all purposes to the same extent that each and every of them is herein incorporated by reference individually.

While the present invention has been particularly shown and described with respect to preferred embodiments thereof, it will be understood by those skilled in the art that the foregoing and other changes in forms and details may be made without departing from the spirit and scope of the invention. It is therefore intended that the present invention not be limited to the exact forms and details described and illustrated but fall within the scope of the appended claims.

What is claimed is:

1. A compound having a structural formula as set forth below, or a salt or ester thereof,

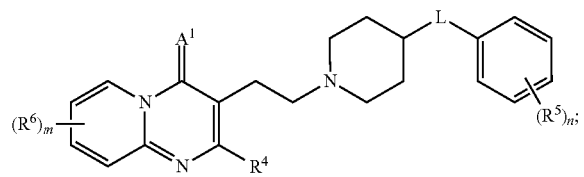

wherein,
$A^1$ is O or S;
L is —C($R^2R^3$)—;
$R^2$ and $R^3$ are each independently hydrogen, halo, alkyl, substituted alkyl, heteroalkyl, substituted heteroalkyl, hydroxyl, alkoxy, amino, alkamino, cyano, or nitro;
$R^4$ is hydrogen, $C_{1-6}$ alkyl, substituted $C_{1-6}$ alkyl, $C_{1-6}$ heteroalkyl, substituted $C_{1-6}$ heteroalkyl, hydroxyl, $C_{1-6}$ alkoxy, amino, or $C_{1-6}$ alkamino;
$R^5$ and $R^6$ are each independently halo, alkyl, substituted alkyl, heteroalkyl, substituted heteroalkyl, hydroxyl, alkoxy, amino, alkamino, cyano, or nitro;
m is an integer of 0, 1, or 2; and
n is an integer of 0, 1, or 2.

2. The compound of claim 1, wherein: $R^4$ is hydrogen, $C_{1-6}$ alkyl, or substituted $C_{1-6}$ alkyl; and each $R^5$ and $R^6$ is independently halo, $C_{1-6}$ alkyl, substituted $C_{1-6}$ alkyl, $C_{1-6}$ heteroalkyl, substituted $C_{1-6}$ heteroalkyl, hydroxyl, alkoxy, amino, alkamino, cyano, or nitro.

3. The compound of claim 1, wherein:
$A^1$ is O;
$R^2$ and $R^3$ are each independently hydrogen, halo, alkyl, substituted alkyl, heteroalkyl, substituted heteroalkyl, hydroxyl, alkoxy, amino, alkamino, cyano, or nitro;
$R^4$ is $C_{1-6}$ alkyl or substituted $C_{1-6}$ alkyl;
each $R^5$ and $R^6$ is independently halo, $C_{1-6}$ alkyl, substituted $C_{1-6}$ alkyl, $C_{1-6}$ heteroalkyl, substituted $C_{1-6}$ heteroalkyl, hydroxyl, alkoxy, amino, alkamino, cyano, or nitro;
m is an integer of 0, 1, or 2; and
n is an integer of 0, 1, or 2.

4. The compound of claim 1, wherein:
$A^1$ is O;
$R^2$ and $R^3$ are each independently hydrogen, halo, alkyl, substituted alkyl, heteroalkyl, substituted heteroalkyl, hydroxyl, alkoxy, amino, alkamino, cyano, or nitro;
$R^4$ is $C_{1-6}$ alkyl or substituted $C_{1-6}$ alkyl;
$R^5$ is halo;
$R^6$ is $C_{1-6}$ alkyl, substituted $C_{1-6}$ alkyl, $C_{1-6}$ heteroalkyl, substituted $C_{1-6}$ heteroalkyl, hydroxyl, alkoxy, amino, alkamino, cyano, or nitro;
m is an integer of 0, 1, or 2; and
n is an integer of 0, 1, or 2.

5. The compound of claim 1, wherein:
$A^1$ is O;
$R^2$ and $R^3$ are each independently hydrogen, halo, alkyl, substituted alkyl, heteroalkyl, substituted heteroalkyl, hydroxyl, alkoxy, amino, alkamino, cyano, or nitro;
$R^4$ is methyl;
$R^5$ is halo; and
m is 0.

6. A pharmaceutical composition, comprising:
a) a therapeutically effective amount of a compound according to claim 1, or a salt or ester thereof; and
b) at least one pharmaceutically acceptable vehicle.

7. The pharmaceutical composition according to claim 6, formulated as: an oral dose formulation, an injection formulation, a transdermal patch formulation, an implantation of a depot formulation, or a topical formulation.

8. The pharmaceutical composition according to claim 6, formulated as a topical formulation.

9. The pharmaceutical composition according to claim 6, formulated as a cream, ointment, jellie, solution, or suspension.

10. The pharmaceutical complition according to claim 6, formulated as a cream.

11. The pharmaceutical composition according to claim 6, formulated as an ointment.

12. The pharmaceutical composition according to claim 6, formulated as a jellie.

13. A topical pharmaceutical composition, comprising:
a) a therapeutically effective amount of a compound selected from the group consisting of:

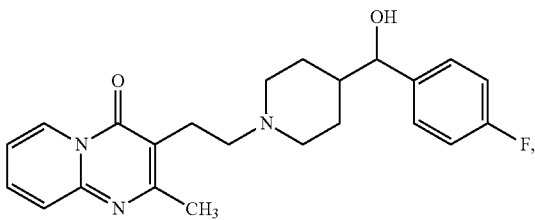

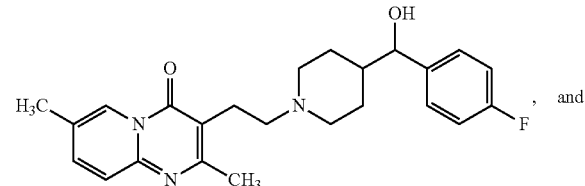

, and

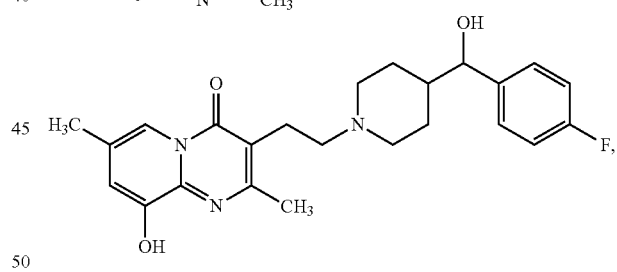

and isomers thereof; and
b) at least one pharmaceutically acceptable vehicle.

14. The topical pharmaceutical composition according to claim 13, wherein the isomer is selected from the group consisting of:

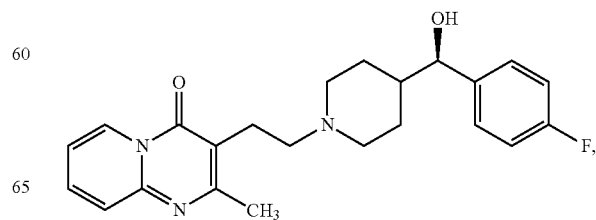

,

-continued

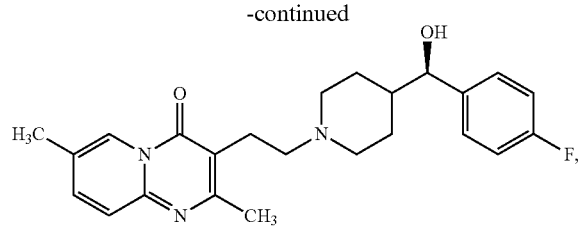

15. The topical pharmaceutical composition according to claim 13, wherein the isomer is selected from the group consisting of:

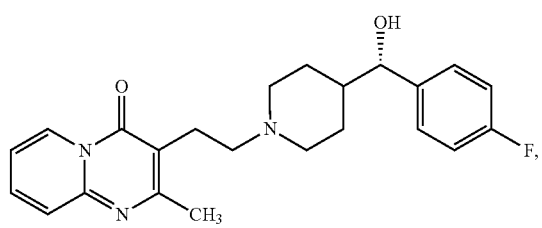

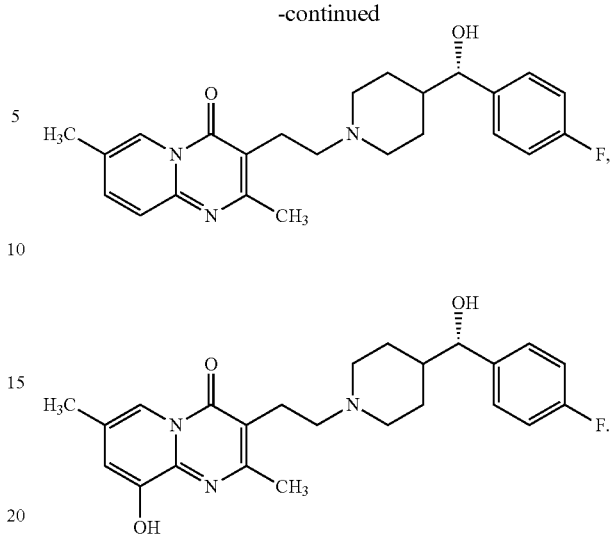

16. The topical pharmaceutical composition according to claim 13, formulated as a cream, ointment, jellie, solution, or suspension.

17. The topical pharmaceutical composition according to claim 13, formulated as a cream.

18. The topical pharmaceutical composition according to claim 13, formulated as an ointment.

19. The topical pharmaceutical composition according to claim 13, formulated as a jellie.

* * * * *